(12) United States Patent
Burkes-Henderson et al.

(10) Patent No.: US 12,350,491 B2
(45) Date of Patent: *Jul. 8, 2025

(54) METHOD FOR DETERMINING FACIAL MUSCLE RESPONSES

(71) Applicant: MARY KAY INC., Addison, TX (US)

(72) Inventors: Shona Burkes-Henderson, Dallas, TX (US); Geetha Kalahasti, Plano, TX (US); David Gan, Southlake, TX (US)

(73) Assignee: MARY KAY INC., Addison, TX (US)

( * ) Notice: Subject to any disclaimer, the term of this patent is extended or adjusted under 35 U.S.C. 154(b) by 26 days.

This patent is subject to a terminal disclaimer.

(21) Appl. No.: 18/221,644

(22) Filed: Jul. 13, 2023

(65) Prior Publication Data

US 2024/0075284 A1 Mar. 7, 2024

Related U.S. Application Data

(63) Continuation of application No. 16/270,211, filed on Feb. 7, 2019, now Pat. No. 11,752,335.

(60) Provisional application No. 62/627,279, filed on Feb. 7, 2018.

(51) Int. Cl.

| | | |
|---|---|---|
| *A61N 1/00* | (2006.01) | |
| *A61B 5/00* | (2006.01) | |
| *A61K 38/48* | (2006.01) | |
| *A61N 1/36* | (2006.01) | |
| *A61Q 19/08* | (2006.01) | |
| *A61K 49/00* | (2006.01) | |
| *A61N 1/04* | (2006.01) | |

(52) U.S. Cl.
CPC ........ *A61N 1/36014* (2013.01); *A61B 5/4519* (2013.01); *A61K 38/4893* (2013.01); *A61Q 19/08* (2013.01); *A61K 49/0006* (2013.01); *A61N 1/0452* (2013.01)

(58) Field of Classification Search
CPC .............. A61N 1/36014; A61B 5/4519; A61K 38/4893; A61Q 19/08
See application file for complete search history.

(56) References Cited

U.S. PATENT DOCUMENTS

| | | |
|---|---|---|
| 6,266,558 B1 | 7/2001 | Gozani et al. |
| 6,688,311 B2 | 2/2004 | Hanim |
| 7,115,399 B2 | 10/2006 | Jenkins |
| 7,140,371 B2 | 11/2006 | Hanin et al. |
| 7,452,335 B2 | 11/2008 | Wells et al. |
| 8,949,033 B2 | 2/2015 | Harakawa et al. |
| 9,162,059 B1 | 10/2015 | Lindenthaler |
| 9,259,576 B2 | 2/2016 | Popovic et al. |
| 11,752,335 B1 * | 9/2023 | Burkes-Henderson ..... A61B 5/4848 607/2 |
| 2005/0241652 A1 * | 11/2005 | Hanin ............ A61K 8/64 128/898 |

FOREIGN PATENT DOCUMENTS

| | | |
|---|---|---|
| EP | 2015065 | 1/2009 |
| WO | WO 03/015829 | 2/2003 |
| WO | WO 2011/160826 | 12/2011 |
| WO | WO 2014/176420 | 10/2014 |

OTHER PUBLICATIONS

Alimohammadi et al. 2013 (Correlation of Botulinum Toxin Dose with Neurophysiological parameters of efficacy and safety in the glabellar muscles: A double-blind, Placebo-controlled, Randomized Study; Acta Derm Venereol, 93: 1-7; (Year: 2013).*

Brandt et al. 2010 (Efficacy and Safety Evaluation of a Novel Botulinum Toxin Topical Gel for the Treatment of Moderate to Severe Lateral Canthal Lines; Dermatological Surgery 36: 2111-2118). (Year: 2010).*

Alimohammadi et al., "Correlation of botulinum toxin dose with neurophysiological parameters of efficacy and safety in the glabellar muscles: a double-blind, placebo-controlled, randomized study," *Acta. Derm. Venereol.*, 2014, 94(1):32-37.

Brandt et al., "Efficacy and Safety Evaluation of a Novel Botulinum Toxin Topical Gel for the Treatment of Moderate to Severe Lateral Canthal Lines" *Dermatological Surgery* 2010, 36: 2111-2118.

Farina et al., "Methods for estimating muscle fibre conducton velocity from surface electromyographic signals" *Med. Biol. Eng. Comput.* 2004, 42:432-445.

Merletti et al., "Technology and instrumentation for detection and conditioning of the surface electromyographic signal: State of the Art" *Clinical Biomechanics* 2009, 24:122-134.

\* cited by examiner

*Primary Examiner* — Mary Maille Lyons
(74) *Attorney, Agent, or Firm* — NORTON ROSE FULBRIGHT US LLP

(57) ABSTRACT

A method for quantitatively assessing muscle contraction of a facial muscle in a person and determining the ability of a treatment material to reduce contraction of the facial muscle is disclosed. The method can include applying an external electrical stimulus to facial skin sufficient to contract a facial muscle, measuring the contractile activity of the contracted facial muscle by measuring the compound motor action potential (CMAP) of the contracted facial muscle to obtain a first average measurement of contractile activity of the contracted facial muscle, administering the treatment material by topically applying the treatment material to the facial skin, and repeating steps (a) and (b) to obtain a second average measurement of contractile activity of the contracted facial muscle.

17 Claims, 3 Drawing Sheets

METHOD FOR DETERMINING FACIAL MUSCLE RESPONSES

CROSS-REFERENCE TO RELATED APPLICATIONS

Figure 1A:
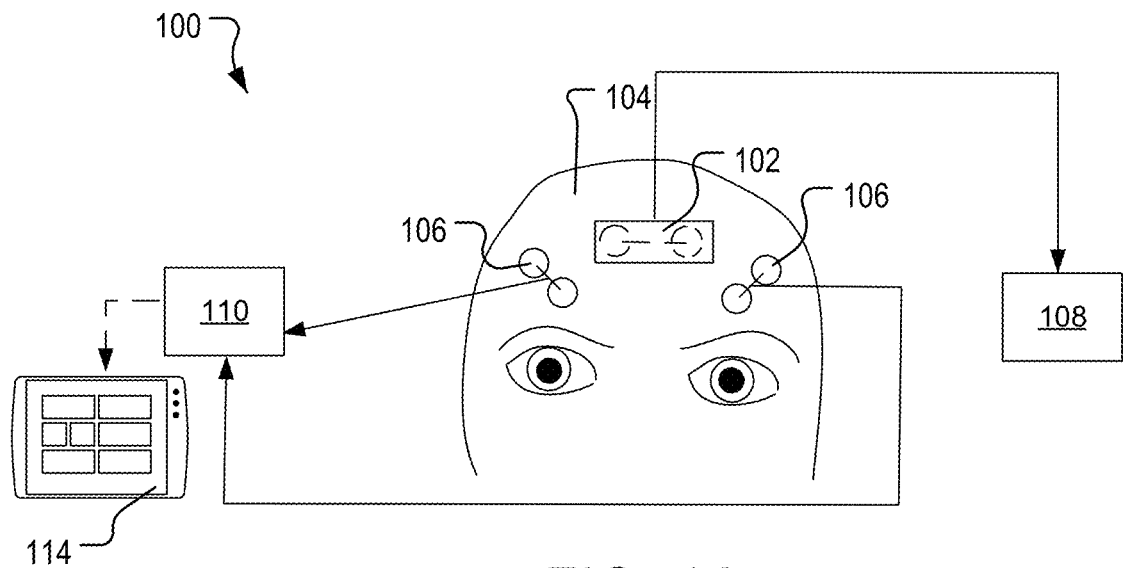

This application is a continuation of U.S. patent application Ser. No. 16/270,211 filed Feb. 7, 2019, which claims the benefit of U.S. Provisional Application No. 62/627,279 filed Feb. 7, 2018. The contents of the referenced applications are incorporated into the present application by reference.

BACKGROUND OF THE INVENTION

A. Field of the Invention

The present invention relates generally to a method for objectively and quantitatively measuring facial muscle contraction in response to a treatment material. This can be used to objectively determine the ability of a treatment material to reduce or suppress facial muscle contraction, and ultimately reduce the appearance of wrinkles.

B. Background

There are certain types of wrinkles that show up on facial skin due to muscle contraction. These types of wrinkles are typically referred to as rhytides, examples of which can include frown or glabellar lines, forehead lines, crow's feet, bunny or nasalis lines, dimpled chin, smile lift lines, lip lines, etc. Currently there are a wide variety of commercially available treatment materials that are said to be effective facial muscle relaxants/muscle contraction suppressants, and are therefore said to be capable of reducing the appearance of such wrinkles. Examples of such materials include injectable neuromodulators such as Botox™ (onabotulinumtoxinA), Dysport™ (abobotulinumtoxinA), or Xeomin™ (incobotulinumtoxinA). Other examples include topically administered treatment materials such as chemical compounds (e.g., gamma-amniobutyric-acid), plant-based materials (e.g., *Acmella oleracea* extracts), and peptides (e.g., acetyl hexapeptide 3).

One of the problems with these treatment materials is the way that such materials are tested. In particular, current methods that are used to measure the degree of contraction of facial muscles are largely based on subjective data rather than objective data. By way of example, the current methods typically rely on a person to make specific facial movements to contract facial muscles such as squinting, frowning, or smiling. The degree and intensity of such movements are subjective and personalized to a given person's physiology. For instance, U.S. Pat. No. 6,688,311 to Hanin and U.S. Pat. No. 7,140,371 to Hanin et al. each describe skin topographical methods. These methods include (1) a skin surface topography profile, (2) a photographic eyebrow position assessment, and/or, (3) an examination of underlying muscle activity in which individuals are asked to elevate their eyebrows and to view an electromyography (EMG) signal to maintain voluntary contractions for 5 seconds at maximum level.

The current methodology used to determine the efficacy of a treatment material to relax facial muscles is based on the subjective movements of the individual being tested. This subjectivity can result in inconsistent and unreproducible results. It can also introduce unwanted variability in the data, making determination of the extent of treatment effects and comparison of treatment modalities difficult.

SUMMARY OF THE INVENTION

The present invention provides a solution to at least some of the problems associated with determining the effectiveness of a given treatment material to relax facial muscles. The solution is premised on a methodology that relies on objective data rather than on the subjective movements of an individual when testing the efficacy of known or potential facial muscle relaxants. In particular, the method of the present invention can utilize an apparatus (e.g., electronic or electrical stimulus bar) that can be attached to facial skin and can be capable of applying a selected and objectively consistent external electrical stimulus to the skin that results in facial muscle contraction. The strength of the electrical stimulus, length of the electrical stimulus, and/or the position of the electrical stimulus on the facial skin can be objectively controlled. Further, these testing parameters can be accurately repeated given that they are based on objective measurements. This can be valuable when testing the effectiveness of a treatment material for relaxing facial muscles/suppressing muscle contraction. Stated another way, the use of an electrical stimulus rather than a user's subjective facial movements provides for more reliable muscle contraction data, which can then be used to objectively determine the effectiveness of a treatment material for relaxing facial muscles/suppressing muscle contraction. Ultimately, a more precise determination of the extent of a given treatment material's ability to relax facial muscles/suppress muscle contraction can be obtained, which can then be used to create reliable active ingredients, injectable compositions, and topical skin compositions for treating skin conditions such as rhytides.

In one aspect of the present invention, there is disclosed a method for quantitatively assessing muscle contraction of a facial muscle. The method can include (a) applying an external electrical stimulus to facial skin sufficient to contract a facial muscle, and (b) measuring the contractile activity of the contracted facial muscle. In a particular instance, the method can be used to determine the ability of a treatment material to reduce contraction of the facial muscle where steps (a) and (b) can be performed to obtain a first measurement of contractile activity of the contracted facial muscle. Subsequently, the treatment material can be administered to the facial skin and steps (a) and (b) can be performed again to obtain a second measurement of contractile activity of the contracted facial muscle. A decrease in contractile activity based on the second measurement as compared to the first measurement can indicate that the treatment material can have facial muscle relaxant properties when administered to facial skin and can therefore be effective at reducing the appearance of rhytides on skin. Steps (a) and (b) can be performed to obtain the first measurement prior to administration of the treatment material to the person's skin, which can allow for a baseline or pre-treatment muscle contraction measurement. Steps (a) and (b) can be repeated for any desired number of times prior to administration of the treatment material. The second measurement of contractile activity can be performed during administration of the treatment material and/or after (e.g., 30 second, 1 minutes, 10 minutes, 30 minutes, 1 hour, 2 hours, 6 hours, 12 hours, 18 hours, 1 day, 2 days, 3 days, 1 week, 2 weeks, etc., after) administration of the material. Administration of the treatment material can be topical such as by topically applying the material to skin (e.g., rubbing or spraying or spreading the material onto the surface of the skin). Administration of the treatment material can be by injection, such as by intradermal, subcutaneous, or intramuscular injection.

The treatment material to be tested for muscle relaxant properties can be a chemical compound, a protein, a peptide, a botanical plant/plant part or extract thereof, or a bacteria, or combinations thereof. Treatment materials include materials known to have muscle relaxant properties and those materials not currently known to have muscle relaxant properties. In this sense, treatment materials encompasses both known muscle relaxants and targeted or proposed treatment materials that ultimately may be discovered as having or as not having muscle relaxant properties. In one instance, the protein can be *Clostridium botulinum* toxin or a derivative thereof. Other known muscle relaxants or treatment materials not currently known to have muscle relaxant properties can be tested in the context of the present invention. Further, the treatment material can be comprised in a topical skin formulation. The topical skin formulation can be structured as an emulsion (e.g., water-in-oil emulsion or an oil-in-water emulsion), a gel (e.g., hydrogel, alcoholic based gel, etc.), an ointment, a solution (e.g., aqueous solution, alcoholic solution, aqueous-alcoholic solution, etc.), or a dispersion. If administered through injection, the injection formulation can also be structured as an emulsion (e.g., water-in-oil emulsion or an oil-in-water emulsion), a gel (e.g., hydrogel, alcoholic based gel, etc.), an ointment, a solution (e.g., aqueous solution, alcoholic solution, aqueous-alcoholic solution, etc.), or a dispersion.

The method of the present invention can further include obtaining at least a first image of the facial skin and at least a second image of the facial skin. The first image can be obtained prior to administering the treatment material to the skin. The first image can also be obtained prior to, during, or after the first measurement of contractile activity. The second image of the facial skin can be obtained after administering the treatment material, and preferably after obtaining the second measurement of contractile activity. Third, fourth, fifth, sixth, or more images can be obtained in the context of the present invention. In some instances, the first image can be a first silicone reverse image and the second image can be a second silicone reverse image. In other instances, the first image can be a first digital image and the second image can be a second digital image. The first and second images and optionally additional images can be used to determine the effectiveness of the treatment material being tested to relax facial skin muscles or, preferable, to reduce the appearance of rhytides present on the facial skin.

In some aspects of the present invention, measuring the contractile activity of the contracted facial muscle can include measuring the electrical activity of the contracted facial muscle. This can be through measuring the compound motor action potential (CMAP) of the contracted facial muscle or through surface electromyography (sEMG). By using sEMG, the electrical activity of individual muscles or muscle groups can be detected, amplified, and/or analyzed. In particular, sEMG can involve the detection, recording, and interpretation of the electric activity of muscles at rest (i.e., static) and during activity (i.e., dynamic). sEMG typically uses a single or an array of electrodes placed on the skin surface over the muscles to be tested. Recording can also be made using a hand-held device, which can be applied to the skin surface at different sites. Electrical activity can be assessed by computer analysis of the frequency spectrum, amplitude, and/or root mean square of the electrical action potential.

The electrical stimulus used to generate facial muscle contraction can be produced from an apparatus that can be attached to the surface of the skin at least partially over or closely located to a muscle to be contracted. The electrical stimulus can generate an electrical current to a nerve or to the muscle to contract the muscle. The apparatus can include conductive material (e.g., electrodes) that can be attached to the skin. The apparatus can also include a power source (e.g., a battery) or connected to a power source for generating the electrical current. A portion of the apparatus that contacts the skin can have any desired shape, including, for example, a square shape, a rectangular shape, a bar shape, a circular shape, a triangular shape, or any other type of desired shape. In some instances, the shape of the conductive material contacting the skin can substantially correspond to the shape of the facial muscle. The electrical stimulus can be applied at a substantially consistent intensity, current, frequency, or duration, or combinations thereof. These parameters can be modified as desired to produce a desired muscle contraction. In some embodiments, the amount of electricity applied to the skin to contract a given facial muscle can be 1 millivolts (mV) to 20 mV, preferably 1 mV to 15 mV, or more preferably 2 mV to 10 mV at 1 to 6 second intervals, preferably 1 to 5 second intervals, or more preferably from 1 to 4 second intervals, or 2 to 4 second intervals. In some preferred aspects, the amount of electricity can be 2 mV to 10 mV at about 2-4 second intervals for a time period of 5 seconds to 60 seconds, preferably 10 seconds to 50 seconds, or more preferably 15 seconds to 40 seconds, or even more preferably 20 seconds to about 35 seconds. Parameters between and outside these ranges are also contemplated (e.g., 1, 2, 3, 4, 5, 6, 7, 8, 9, 10, 11, 12, 13, 14, 15, 16, 17, 18, 19, or 20, or more mV and/or 1, 2, 3, 4, 5, 6 or more second intervals, and/or overall time period of 5, 10, 15, 20, 25, 30, 35, 40, 45, 50, 55, 60, or more seconds). By using these parameters, one can obtain an average measurement of contractile activity. In some preferred aspects, the methods of the present invention can include identifying an optimal electrical stimulus and then using the optimal electrical stimulus to stimulate the facial muscle. By way of example, and as illustrated in a non-limiting manner in the Examples, identifying an optimal electrical stimulus can include applying 2 mV to 10 mV of electricity to the skin at about 2 second intervals starting at 2 mV and increasing up to 10 mV and measuring the compound motor action potential (CMAP) for each stimulus. These data can then be used to identify the optimal strength (in mV) of the electrical stimulus (e.g., by analyzing the shape of the CMAP response curve). Subsequently, the optimal stimulus strength can be used with the methods of the present invention to perform steps (a) (applying an external electrical stimulus to facial skin sufficient to contract a facial muscle) and (b) (measuring the contractile activity of the contracted facial muscle). In some preferred instances, step (a) can include stimulating the facial muscle with the optimal stimulus strength over X number of times at Y second intervals. X can be 1 to 20, 2 to 20, 3 to 20, 4 to 20, 5 to 15, 7 to 12, or preferably about 9 to 11, or even more preferably about 10. Y can be 1 to 10 seconds, 1 to 9 seconds, 1 to 8 seconds, 1 to 7 seconds, 1 to 6 seconds, 1 to 5 seconds, preferably 2 to 5 seconds, or more preferably about 2 to 4 seconds, or even more preferably about 3 seconds. As noted above, this can allow one to obtain an average measurement of contractile activity. In some particularly preferred embodiments, the facial skin can include a rhytide, which would allow the direct testing of a treatment material's ability to reduce the appearance of a rhytide present on a person's skin.

It is contemplated that any facial muscle can be used with the methods of the present invention. In some particular aspects, the facial muscle to be contracted is a glabellar complex muscle, an orbicularis oculi muscle, a depressor muscle (e.g., anguli oris, depressor septi, or depressor labii inferioris, or any combination thereof), or a frontalis muscle, or any combination thereof. Still further, while preferred embodiments of the present invention use facial muscle contraction, it is contemplated that the methods of the present invention can be used for other non-facial muscles (e.g., muscles in the hands, arms, shoulders, neck, back, torso, abdomen, legs, feet, etc.).

Also contemplated in the context of the present invention is a kit for quantitatively assessing muscle contraction of a facial muscle. The kit can include an external electrical stimulus apparatus capable of providing an electrical stimulus to facial skin sufficient to contract a facial muscle and an apparatus for measuring the contractile activity of the contracted facial muscle. In some preferred embodiments, the apparatus for measuring the contractile activity of the contracted facial muscle can be a surface electromyography device. The kit can also include the treatment material to be applied to the facial skin so as to determine the ability of the treatment material to reduce contraction of the facial muscle.

Also disclosed in the context of the present invention are aspects 1-36. Aspect 1 is a method for quantitatively assessing muscle contraction of a facial muscle, the method comprising, (a) applying an external electrical stimulus to facial skin sufficient to contract a facial muscle, and (b) measuring the contractile activity of the contracted facial muscle. Aspect 2 is the method of aspect 1, wherein the method is used to determine the ability of a treatment material to reduce contraction of the facial muscle. Aspect 3 is the method of aspect 2, wherein steps (a) and (b) are performed to obtain a first measurement of contractile activity of the contracted facial muscle, and then the treatment material is administered to the facial skin and steps (a) and (b) are performed again to obtain a second measurement of contractile activity of the contracted facial muscle, wherein a decrease in contractile activity based on the second measurement as compared to the first measurement indicates that the treatment material can reduce contraction of the facial muscle when administered to the facial skin. Aspect 4 is the method of aspect 3, wherein the electrical stimulus comprises application of 2 mV to 10 mV of electricity. Aspect 5 is the method of aspect 4, wherein the electrical stimulus is applied at 2 to 4 second intervals for 5 to 15 intervals to obtain an average measurement of contractile activity of the facial muscle. Aspect 6 is the method of aspect 5, wherein measuring the contractile activity of the contracted facial muscle comprises measuring the compound motor action potential (CMAP) of the contracted facial muscle. Aspect 7 is the method of any one of aspects 3 to 6, wherein the treatment material is administered by topically applying the treatment material to the facial skin. Aspect 8 is the method of any one of aspects 3 to 6, wherein the treatment material is administered by injecting the treatment material into the facial skin. Aspect 9 is the method of aspect 8, wherein the injection is intradermal, subcutaneous, or intramuscular. Aspect 10 is the method of any one of aspects 2 to 9, wherein the treatment material comprises a chemical compound, a protein, a peptide, a botanical plant/plant part or extract thereof, or a bacteria, or combinations thereof. Aspect 11 is the method of aspect 10, wherein the treatment material is a protein. Aspect 12 is the method of aspect 11, wherein the protein is *Clostridium botulinum* toxin or a derivative thereof. Aspect 13 is the method of any one of aspects 2 to 12, wherein the treatment material is comprised in a topical skin formulation selected from an emulsion, a gel, an ointment, or a solution. Aspect 14 is the method of aspect 13, wherein the topical skin formulation is an oil-in-water emulsion. Aspect 15 is the method of any one of aspects 2 to 14, further comprising obtaining a first image of the facial skin prior to administering the treatment material and obtaining a second image of the skin after administering the treatment material, and preferably after obtaining the second measurement of contractile activity. Aspect 16 is the method of aspect 15, wherein the first image is a first silicone reverse image and the second image is a second silicone reverse image. Aspect 17 is the method of aspect 15, wherein the first image is a first digital image and the second image is a second digital image. Aspect 18 is the method of any one of aspects 15 to 17, wherein the first and second images are used to determine the effectiveness of the treatment material to reduce the appearance of rhytides present on the facial skin. Aspect 19 is the method of any one of aspects 1 to 18, wherein measuring the contractile activity of the contracted facial muscle comprises measuring the electrical activity of the contracted facial muscle. Aspect 20 is the method of any one of aspects 1 to 19, wherein measuring the contractile activity of the contracted facial muscle comprises measuring the compound motor action potential (CMAP) of the contracted facial muscle. Aspect 21 is the method of any one of aspects 1 to 20, wherein measuring the contractile activity of the contracted facial muscle comprises surface electromyography. Aspect 22 is the method of any one of aspects 1 to 21, wherein the external electrical stimulus provides an electrical current to a nerve or muscle capable of contracting the muscle. Aspect 23 is the method of any one of aspects 1 to 22, wherein the external electrical stimulus is generated from a conductive material, preferably having a square shape, a rectangular shape, a circular shape, or a triangular shape, and more preferably a square or rectangular shape. Aspect 24 is the method of any one of aspects 1 to 22, wherein the external electrical stimulus is generated from a conductive material having a shape that substantially corresponds to the shape of the facial muscle. Aspect 25 is the method of any one of aspects 1 to 24, wherein the external electrical stimulus is applied at a substantially consistent intensity, current, frequency, or duration, or combinations thereof. Aspect 26 is the method of any one of aspects 1 to 25, wherein the facial muscle is a glabellar complex muscle, an orbicularis oculi muscle, a depressor muscle, or a frontalis muscle, or any combination thereof. Aspect 27 is the method of aspect 26, wherein the facial muscle is the glabellar complex muscle. Aspect 28 is the method of aspect 26, wherein the facial muscle is the orbicularis oculi muscle. Aspect 29 is the method of aspect 26, wherein the facial muscle is the frontalis muscle. Aspect 30 is the method of aspect 26, wherein the facial muscle is the depressor muscle selected from depressor anguli oris, depressor septi, or depressor labii inferioris, or any combination thereof. Aspect 31 is the method of any one of aspects 1 to 30, wherein the facial skin includes a rhytide. Aspect 32 is the method of any one of aspects 1 to 31, wherein an optimal external electrical stimulus is determined prior to performing step (a), wherein the optimal external electrical stimulus is used in performing step (a), and wherein the optimal external electrical stimulus corresponds to the maximum contractile activity of the facial muscle. Aspect 33 is the method of aspect 32, wherein the optimal external electrical stimulus is obtained by applying an increasing amount of voltage at periodic intervals to facial skin sufficient to contract the facial muscle.

Aspect 34 is a kit for quantitatively assessing muscle contraction of a facial muscle, the kit comprising (a) an external electrical stimulus apparatus capable of providing an electrical stimulus to facial skin sufficient to contract a facial muscle, and (b) an apparatus for measuring the contractile activity of the contracted facial muscle. Aspect 35 is the kit of aspect 34, wherein the apparatus for measuring the contractile activity of the contracted facial muscle is a surface electromyography device. Aspect 36 is the kit of aspect 35, further comprising a treatment material to be applied to the facial skin so as to determine the ability of the treatment material to reduce contraction of the facial muscle.

It is contemplated that any embodiment discussed in this specification can be implemented with respect to any method or composition of the disclosure, and vice versa. Furthermore, compositions of the disclosure can be used to achieve methods of the disclosure.

"Topical application" means to apply or spread a composition onto the surface of lips or keratinous tissue. "Topical skin composition" includes compositions suitable for topical application on skin and/or keratinous tissue. Such compositions are typically dermatologically-acceptable in that they do not have undue toxicity, incompatibility, instability, allergic response, and the like, when applied to skin and/or keratinous tissue. Topical skin care compositions of the present disclosure can have a selected viscosity to avoid significant dripping or pooling after application to skin and/or keratinous tissue.

"Clostridial neurotoxin" means a neurotoxin produced or obtained from, or native to, a Clostridial bacterium, such as *Clostridium botulinum*, *Clostridium butyricum* or *Clostridium* beratti. Clostridial neurotoxin also includes neurotoxin made recombinantly by a non-Clostridial species or a modified Clostridial toxin such that the toxin can have at least one of its amino acids deleted, modified or replaced, as compared to a native Clostridial toxin. Thus, the Clostridial toxin used can be a recombinantly produced Clostridial (e.g., botulinum) toxin or a derivative or fragment thereof. A botulinum toxin used in a method according to the present invention can be a botulinum neurotoxin. Clostridial neurotoxin can be obtained from Allergan (U.S.A.) under the trade name BOTOX®.

*Acmella Oleracea* extract is an alcohol (propanediol) and/or water extract of the whole plant. The plant is predominately found in Madagascar and the Mascarene Islands. *Acmella Oleracea* extract can be obtained from Gattefosse under the trade name Gatuline® Expression AF.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase to achieve a desired result. By way of example, a treatment material that is capable of relaxing a muscle (e.g., a facial muscle) can reduce contraction of the muscle. By comparison, a treatment material that is capable of stimulating muscle contraction of a given muscle (e.g., a facial muscle) can promote contraction of said muscle.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The assays and methods for their use can "comprise," "consist essentially of," or "consist of" any of the ingredients or steps disclosed throughout the specification. With respect to the phrase "consisting essentially of," a basic and novel property of the methods of the present invention is the ability to quantitatively measure the ability of a given treatment material to reduce contraction of a muscle (e.g., a facial muscle).

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

Advantages of the present invention may become apparent to those skilled in the art with the benefit of the following detailed description and upon reference to the accompanying drawings.

FIGS. 1A and 1B depict schematics of a person being tested using a method of the present invention.

FIG. 2 provides an illustration of the areas on a person's face where a method of the present invention was performed.

FIG. 3A typical placement of the EMG recording device/sensor and the muscle stimulus bar electrode on a person's face is illustrated in FIG. 3.

FIG. 4 Location of five (5) injection points of Botox™ into the forehead of people.

While the invention is susceptible to various modifications and alternative forms, specific embodiments thereof are shown by way of example in the drawings. The drawings may not be to scale.

DETAILED DESCRIPTION OF THE INVENTION

A discovery has been made that provides a solution to at least some of the problems associated with current methods that are used to determine the muscle relaxant activity of a given treatment material. The solution is premised on the use of qualitative, objective, controllable, and repeatable methods for contracting muscles and for determining the strength of such contraction prior to and after administration of a targeted treatment material. A difference in muscle contraction strength pre- and post-treatment can objectively indicate whether a given treatment material promotes or reduces muscle contraction. Treatment materials that have the ability to reduce muscle contraction can be used to reduce the appearance of wrinkles on skin, especially wrinkles such as rhytides that present on the skin due to muscle contraction.

Non-limiting aspects of these and other aspects of the present invention are provided below with reference to the figures.

Figure 1B:
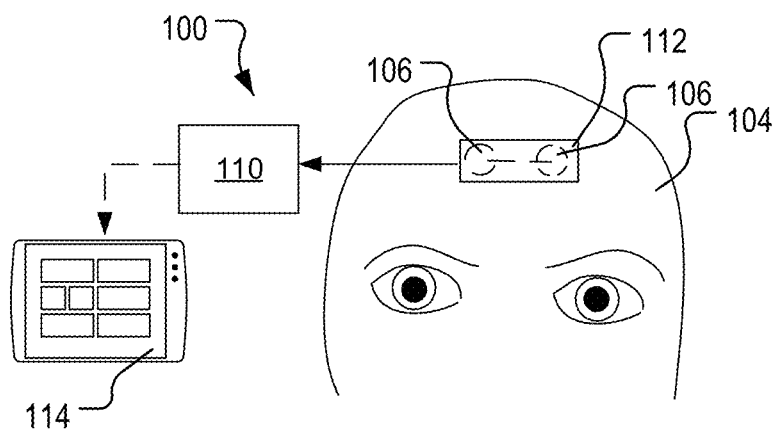

The methods of the present invention can utilize a conductive material capable of applying electrical stimulus to keratinous tissue sufficient to produce a response in a subcutaneous muscle of the face, a power source, and a recording device. FIGS. 1A and 1B are schematics that depict methods using these objects. In step 1 of method 100, the area of the skin to be tested is cleaned to remove impurities (e.g., make-up, lotions, cosmetics, etc.). This can be done with using soap and water followed by drying. In some embodiments, images (e.g., digital images) of the skin area to be tested can be taken for reference. Silicone rubber negative replicas of the skin surface area (e.g., facial area) before and after treatment, which are impressions of the face, can also be taken. In other instances when rhytides are present, the skin area can be given a rating as to the severity of the rhytides (e.g., folds, ridges, or creases in the tissue). For example, the affected area can be rated from 0 to 9 with 0 being no to very few wrinkles and 9 being a significant amount of wrinkles, which can include fine lines. Conductive material 102 can be positioned on a portion of the dried face 104 (e.g., facial tissue) so that a corresponding muscle around or at least partially underneath said conductive material is stimulated. In some embodiments, the conductive material can have a parallelogram shape, preferably a square or rectangle shape. In a particular instance, the conductive material is a bar electrode having flat 9 mm (0.35") contacts with 30 mm (1.2") spacing and fitted with shrouded 4 mm (0.16") connectors. Stimulating bar electrodes that can be used in the context of the present invention are commercially available from a variety of sources (e.g., Ad Instruments Inc., Colorado Springs, CO (USA)). A non-limiting example of a stimulating bar electrode that can be used is a Stimulating Bar Electrode (MLADDF30) (Ad Instruments Inc., Colorado Springs, CO (USA)).

As shown in FIG. 1A, recording electrodes 106 can be positioned on the surface of the face where the subcutaneous muscle is present that is to be monitored. Recording electrodes 106 can be positioned based on a known techniques to capture subcutaneous muscle response. For example, recording electrodes 106 can each be positioned the same distance above the center of each eye, or the same distance from the bridge of the nose. Recording electrodes can be positioned on the face prior to positioning conductive material 102. One of skill in the art of surface electromyography would be able to determine the exact position of the recording electrodes 106. Conductive material 102 can be attached to a power source 108 and recording electrodes 106 can be attached a recording device 110. Recording electrodes 106 and recording device 110 that can be used can be any recording electrodes and devices known in the art. A non-limiting example of a recording electrode is a Trigno™ wireless EMG Sensor (Ad Instruments Inc., Colorado Springs, CO (USA)). A non-limiting example of a recording device 110 is a Tringo™ Wireless Foundation System (Ad Instruments Inc., Colorado Springs, CO (USA)). Power source 108 can be any power source capable of providing energy to the electrode. A non-limiting example of a power source 108 can be a Stimulus Isolator FE155 or Stimulus Isolator FE180 from Ad Instruments Inc., Colorado Springs, CO (USA). In another aspect, and as shown in FIG. 1B, recording electrodes 106 can be incorporated directly into conductive material 112 such that conductive material 112 can both stimulate and record the response of the subcutaneous muscle. In this instance, recording device 110 can act as a power source for conductive material 112 and a recording device for recording electrodes 106 in the conductive material 112. The muscle response can be measured by one or more surface topography techniques. Non-limiting examples of surface topography techniques include examining the change or reduction in a rhytide or rhytides associated with the muscle contraction obtained during surface EMG of the treated areas. Examining a photograph or photographs of wrinkles associated with the muscle contraction can also be performed.

A desired region (e.g., forehead, chin, eyebrow area, check, etc.) of face 104 can be subjected to an electrical stimulus from conductive material 102 (FIG. 1A) or 112 (FIG. 1B), by applying a voltage to the conductive material from power source 108 (FIG. 1A) or 110 (FIG. 1B). Conductive material 102 or 112 can produce a consistent or constant intensity, current, frequency, duration, or combinations thereof. In some embodiments, the amount of current applied to the skin can be 1 millivolts (mV) to 20 mV, preferably 1 mV to 15 mV, or more preferably 2 mV to 10 mV at 1 to 6 second intervals, preferably 1 to 5 second intervals, or more preferably from 1 to 4 second intervals, or even more preferably at 2 to 4 second intervals. In some preferred aspects, the amount of electricity applied through the stimulus can be 2 mV to 10 mV at about 2-4 second intervals for a time period of 5 seconds to 60 seconds, preferably 10 seconds to 50 seconds, or more preferably 15 seconds to 40 seconds, or even more preferably 20 seconds to about 35 seconds. Parameters between and outside these ranges are also contemplated (e.g., 1, 2, 3, 4, 5, 6, 7, 8, 9, 10, 11, 12, 13, 14, 15, 16, 17, 18, 19, or 20, or more mV and/or 1, 2, 3, 4, 5, 6 or more second intervals, and/or overall time period of 5, 10, 15, 20, 25, 30, 35, 40, 45, 50, 55, 60, or more seconds). By using these parameters, one can obtain an average measurement of contractile activity. In some preferred aspects, the methods of the present invention can include identifying an optimal electrical stimulus and then using the optimal electrical stimulus to stimulate the facial muscle. By way of example, and as illustrated in a non-limiting manner in the Examples, identifying an optimal electrical stimulus can include applying 2 mV to 10 mV of electricity to the skin at about 2 second intervals starting at 2 mV and increasing up to 10 mV and measuring the compound motor action potential (CMAP) for each stimulus. These data can then be used to identify the optimal strength (in mV) of the electrical stimulus (e.g., by analyzing the shape of the CMAP response curve). In some preferred instances the optimal strength corresponds with the strongest CMAP response. Application of an electrical stimulus can cause a subcutaneous muscle to respond (e.g., contract), and the response can be recorded by recording device 110 during or after the electrical stimulus is applied. The application of electrical stimulus and recordation of muscle response can be repeated at least two times, preferably up to 10 or 15 times to obtain sufficient data as a reference (base-line) measurement. The recorded data can be analyzed using mean-squared error (MSE) and root MSE (RMSE) methodology. The results can be displayed on a display screen of recording device 110, sent to a computer terminal through a data connection, or displayed on a hand held device 114 (e.g., phone, slate, or the like).

The affected referenced skin area (e.g., skin having a rhytide) can be treated with the treatment material (e.g., rhytide treatment agent). Non-limiting examples of treatment materials include injectable neuromodulators such as Botox™ (onabotulinumtoxinA), Dysport™ (abobotulinumtoxinA), or Xeomin™ (incobotulinumtoxinA). Other examples include topically administered materials such as chemical compounds (e.g., gamma-amniobutyric-acid), plant-based materials (e.g., *Acmella oleracea* extracts), and peptides (e.g., acetyl hexapeptide 3). *Clostridium botulinum*, Botox® (Allergan, USA). It is also contemplated in the context of the present invention that the methods disclosed can be used on known and unknown treatment materials. If the methods are used on known treatment materials, then the methods of the present invention can advantageously provide a more objective and reliable muscle contraction profile of the known treatment material. If the methods are used on unknown treatment materials, then the methods of the present invention can advantageously identify materials that have muscle relaxant properties. "Unknown treatment materials" can include chemical compounds, plant based materials, peptides, proteins or other any other materials that may be currently known to be used in injectable or topical formulations but that are not known to have muscle relaxant properties. "Unknown treatment materials" can also include chemical compounds, plant based materials, peptides, proteins or other any other materials that have not yet been developed as of the filing date of the present application. One of the unique aspects of the present invention is that it provides an objective and reliable methodology or assay for testing any types of materials for muscle relaxant properties. Therefore, all materials currently used in injectable formulations or topical skin formulations or other types of formulations can be considered a treatment material in the context of the present invention. Treatment can include local administration of the treatment material (e.g., intradermal, subcutaneous, or intramuscular injection) to a nerve or muscle to the affected area (e.g., to a rhytide) and/or topical application of the treatment material to skin that includes a rhytide and/or to skin that may present a rhytide due to muscle contraction or to an area of the skin that is in close proximity to a muscle that is associated with the rhytide. After treatment, method 100 can be repeated after a specified period of time to obtain measurements of the same muscle group previously measured. In some instances, 1, 2, 3, 4, 5, 6, 7, 8, 9, 10, or more measurements can be performed to obtain accurate data. Images and silicone mask reverse images can also be obtained, but are not required. In some embodiments, the treated area is rated 0 to 9 as previously described. Non-limiting examples of time periods after the initial treatment in which a subsequent treatment can occur can be 1, 2, 3, 6, 12, or 18 hours, 1, 2, 3, 4, 5, or 6 days, or 1, 2, or 3 weeks, or 1, 2, 3, 4, 5, 6, 7, 8, 9, 10, or 11 months, or longer. In some instances, the facial area is treated 2 days after the initial treatment, 2 weeks after the initial treatment, and then 4 weeks after the initial treatment. The time period of the treatment and method 100 being performed can be determined by person administering or in charge of the treatment method. Further, after every subsequent treatment, a measurement on muscle contraction can be obtained by using the methods of the present invention. Having multiple rounds of treatment and multiple measurements on muscle contraction can be helpful in determining the efficacy of a given treatment period over a given time interval.

The data obtained from the post-treatment measurements can be analyzed using mean-squared error (MSE) and root MSE (RMSE) methodology and compared to the obtained pre-treatment reference. Difference in the pre- and post-treatment data can be useful in determining the effectiveness of the treatment. Muscle contraction characteristics and/or rhytide characteristics that are reduced can indicate that the treatment material has muscle relaxing properties/can reduce muscle contraction. By comparison, muscle contraction characteristics and/or rhytide characteristics that remain the same can indicate that the treatment material has no muscle relaxing properties. Still further, muscle contraction characteristics and/or rhytide characteristics that are increased can indicate that the treatment material can stimulate muscle contraction. With respect to rhytides, the pre- and post-treatment data comparison can include comparing the depth, length, width, surface area, number of rhytides, density, and the like, pre- and post-treatment. By way of example, analysis of curve area and peak height sEMGs recordings obtained prior and after treatment can be compared. A reduction in cure area and peak height can indicate that the treatment was successful or is being maintained (i.e., an additional treatment is not necessary). The results can be printed, displayed on a display screen of recording device 110, sent to a computer terminal through a data connection, and displayed on a hand held device (e.g., phone, tablet, or the like) 114.

While FIGS. 1A and 1B reference facial skin and facial muscles, the methods of the present invention can be used on other areas of a person's body (e.g, hands, arms, shoulders, back, torso, neck, legs, feet, etc., and the corresponding muscles associated with said body parts). That is, the methods of the present invention that can help objectively determine the efficacy of treatment material in reducing/suppressing muscle contraction can be used with a wide variety of muscles in a person's body. The methods of the present invention are not limited to facial muscle contraction; they can be extended to other muscles of the body.

Non-limiting examples of facial muscle responses that can be analyzed using the methods of the present invention include responses of facial muscles of the glabellar complex, orbicularis muscles, frontalis muscles, or depressor anguli oris muscles, or combinations thereof. The muscles of the glabellar complex can be responsible for formation of frown lines that include the corrugator supercilii, depressor supercilii, procerus, and orbicularis oculi para frontalis muscles. The corrugator supercilii lies below the frontalis muscle and functions to draw the brow medially and downward, whereas the smaller depressor supercilii can be located lower than the corrugator muscle and functions to draw the medial brow downward. The procerus can be located between the eyebrows and also works to depress the glabellar medial brow region. The depressor function of the glabellar complex is opposed by the frontalis muscle. This muscle is merged with the superior portions of the glabellar complex, from which it extends upwards underneath the forehead. The frontalis muscle is a muscle of the forehead and is associated with raising of the brow. The orbicularis muscle is a muscle that closes the eyelids. The depressor anguli oris muscle is a facial muscle associated with frowning. In a preferred aspect, contractile activity is measured.

A. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

1. Example 1 (Determining the Repeatability and Reproducibility of Facial Electromyography Measurements in a Population of Healthy Adult Females: A Development Protocol)

Objective: The objective of this study was to determine the intra and inter-subject variability associated with surface electromyography (sEMG) measurements taken at four different locations on the face (i.e., muscle groups) within each subject by three different clinicians:
 (1) Glabellar/Frown lines between the eyebrows area (focusing on the corrugator supercilii muscle and procerus muscle;
 (2) Forehead/Worry lines area (focusing on the frontalis muscle);
 (3) Canthi/peri-orbital/Smile lines area (focusing on the orbicularis oculis); and
 (4) Marionette/frown lines near the corners of the mouth area (focusing on the depressor anguli oris muscle.

Figure 2:
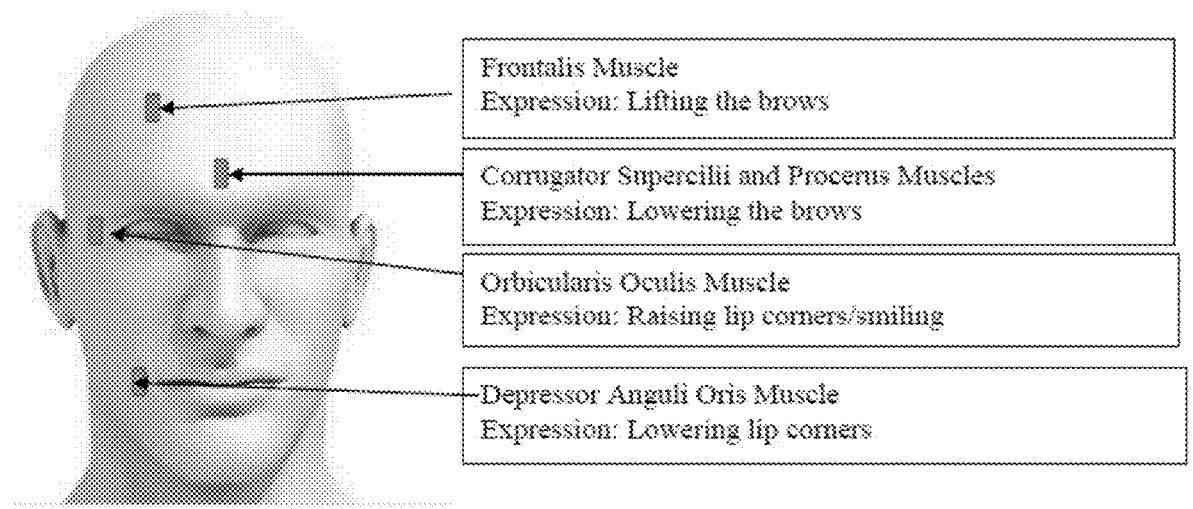

Materials and Methods: Day 1—Thirteen (13) females, ranging in age from 41 to 65 years, were asked to wash their face with a standard cleanser and then directed to an environmentally controlled room (70° F.±5° F. (21±1.5° C.); 50%+15% relative humidity) where they equilibrated for at least 15 minutes. Following equilibration, a technician applied a Trigno™ wireless EMG Sensor (Ad Instruments Inc., Colorado Springs, CO (USA)) to each of the above noted areas (one sensor was used by moving the sensor to each area after completion of measurements at that test site). FIG. 2 provides an illustration of the tested areas. At each test site, the subjects were asked to perform facial expressions to help identify the location of wrinkling. Once the sensor was attached to the subject, a series of "insult" scans were generated at two second intervals in which the amount of stimulus/energy/insult (measured in millivolts, mV) varied at each interval (starting at 2 mV) and increasing up to a maximum of 10 mV). The stimulus was induced by placing a stimulating bar electrode in the area close to the Trigno™ sensor and powering the bar with a set energy (mV). A Stimulating Bar Electrode (MLADDF30) (Ad Instruments Inc., Colorado Springs, CO (USA)) was used for the electrode, and a Stimulus Isolator FE180 (Ad Instruments Inc., Colorado Springs, CO (USA)) was used to provide the energy/power to the electrode. The scans were reviewed after each insult to determine if proper compound motor action potential (CMAP) was observed. After the position of the stimulating bar (relative to the Trigno™ sensor) and stimulus strength were identified that produces the proper CMAP response, these values were recorded for that site and used throughout the study (for that site). The recording device used was a Tringo™ Wireless Foundation System (Ad Instruments Inc., Colorado Springs, CO (USA)). The stimulus was set to the mV that produced the best CMAP response (based on the shape of the curve) and a total of 10 sequential scans were taken over a 33 second period with stimulus of the test site occurring every three seconds. Once the 10 scans were completed for the first site, the process was repeated at the next site as described above until all sites have been evaluated. Once all sites were measured, the subjects were instructed to return to the testing facility the following day for additional measurements.

Day 2—Subjects arriving on Day 2 were instructed to wash their face with the provided cleanser, pat dry and then directed into an environmentally controlled room (70° F.+5° F.; 50%+15% relative humidity) to equilibrate for at least 15 minutes. Information regarding any changes in the subject's health history were captured and an adverse event form was completed for those subjects who reported safety-related comments (i.e., skin irritation at test sites). Following equilibration, the same four sites measured on Day 1 were repeated using the same placement of the Trigno™ sensors and stimulating bar and using the same stimulus (mV) as determined on the previous day for that site. Any additional changes made to the baseline parameters were recorded on the subject's data sheet. Once all four sites were measured by a technician, two additional technicians independently measured the same sites such that on Day 2, three technicians (same technician as on Day 1 plus two different technicians) performed measurements on all four test sites. At the end of all Day 2 activities subjects were instructed to return the following day.

Day 3—Subjects arriving on Day 3 were instructed to wash their face with the provided cleanser, pat dry and then directed into an environmentally controlled room (70° F.+5° F.; 50%+15% relative humidity) to equilibrate for at least 15 minutes. Information regarding any changes in the subject's health history were captured and an adverse event form was completed for those subjects who report safety-related comments (i.e., skin irritation at test sites). Following equilibration, the same four sites measured on Day 1 were repeated using the same placement of the Trigno™ sensors and stimulating bar and using the same stimulus (mV) as determined on the previous day for that site. Once all four sites were measured by a technician, two additional technicians independently measured the same sites such that on Day 3, three technicians (same technicians as on Day 1 plus the two technicians from Day 2) performed measurements on all four test sites. After Day 3 measurements subjects were dismissed from the study.

Results: In order to determine the variability between technician and measurements sites (i.e., facial muscle groups), the EMG data were analyzed with emphasis placed on the mean squared error (MSE) of the values and the root-MSE. The MSE is a measure of how close the data points are to a fitted line or how "accurate" the data points are to an estimator. The lower the MSE, the less variability observed from one technician to the next. If the MSE is zero, there is no variability and the estimator predicts observations. Therefore, values close to zero would indicate small variability (high precision).

Table 1 shown below displays the inter-technician differences in the root MSE for both the Area Under the Curve (AUC) and Peak Height of the curve generated from the stimulus of the various muscle groups measured. The Table 1 data shows the variability in measurements for both AUC and Peak Height, from one day to the next within subjects and from one technician to the next. For AUC, technicians 1 and 3 were the closest with the least variability. For peak height, technicians 2 and 3 were the closest with the least variability. However, the data for all of the technicians were close and while there may be differences, the differences are small and would indicate that little variability exists between technicians.

TABLE 1

(Inter-technician differences in the root mean square error mean by parameter and location)

| Muscle | Technicians 1 | 2 | 3 | 1 minus 2 | 1 minus 3 | 2 minus 3 |
|---|---|---|---|---|---|---|
| AUC | | | | | | |
| Depressor | 0.29399 | 0.50329 | 0.29134 | −0.2095 | 0.00265 | 0.21195 |
| Frontalis | 0.67546 | 0.52933 | 0.87116 | 0.14613 | −0.19570 | −0.34183 |
| Glabellar | 0.40289 | 0.36968 | 0.78246 | 0.03321 | −0.37957 | −0.41278 |
| Orbicular | 0.40225 | 0.26942 | 0.35791 | 0.13283 | 0.04434 | −0.08849 |
| | | | Mean | −6.52536 | −1.42332 | 5.102048 |
| Peak Height | | | | | | |
| Depressor | 5.12044 | 6.92066 | 5.51734 | −1.80022 | −0.3969 | 1.40332 |
| Frontalis | 8.86843 | 9.80005 | 11.37341 | −0.93162 | −2.50497 | −1.57336 |
| Glabellar | 7.5274 | 6.43105 | 10.44185 | 1.09635 | −2.91445 | −4.0108 |
| Orbicular | 5.88728 | 6.34882 | 5.94737 | −0.46154 | −0.06009 | 0.40145 |
| | | | Mean | −1.38703 | −0.98498 | 0.402045 |

Table 2 shown below displays a summary of the square root of the mean variance for both AUC and Peak Height for all four muscle groups measured. The Table 2 data show the depressor muscle to have the lowest square root of the mean variance; however, all muscle groups are relatively close to each other.

TABLE 2

(Square root of the mean variance from the intra-technician mean scores by parameter and location)

| Parameter | Location | Square Root of the Mean Variance |
|---|---|---|
| AUC | Depressor | 0.2845 |
| AUC | Frontalis | 0.6754 |
| AUC | Glabellar | 0.3931 |
| AUC | Orbicular | 0.4020 |
| Peak Height | Depressor | 4.9264 |
| Peak Height | Frontalis | 8.8684 |
| Peak Height | Glabellar | 7.4411 |
| Peak Height | Orbicular | 5.9913 |

The results obtained in this study can be analyzed in terms of two points: Whether there was sufficient reproducibility between technicians taking measurements on the same subject, and which site had the most consistent measurements between different technicians. Considering the low values of the RMSE, the data supports the conclusion that the variability between technician and site is small and that the EMG measurements tend to be consistent between technician and sites. With respect to ease of measurement, the glabellar and depressor muscles are the easiest to measure as there is more space to place the probes. The Frontalis muscle can be challenging with individuals with small foreheads and the orbicularis can be close to the hairline which can interfere with measurements.

2. Example 2 (Single Center Clinical Trial to Determine the Ability of an Electromyography Instrument to Measure Muscle Contraction in Facial Muscles Treated with Botox™)

Objective: The primary objective was to determine the ability of an electromyography (EMG) instrument (AD Instruments, Colorado Springs, CO.) to measure changes in the compound motor action potential (CMAP) of facial muscles (glabella muscles: Corrugator Supercilii and Procerus Muscles) when said muscles were injected with a material (Botox™, Allergan, Inc.) known to decrease CMAP. The secondary objective was to compare the EMG technology to the standard clinical/consumer evaluations for wrinkle evaluation.

Test Product Identification: Botox (Onabotulinumtoxin A) from Allergan, Inc., was used for this study.

Subjects: Six (6) subjects were enrolled in the study, five (5) of which completed the study. Subjects were normal, healthy females from 55 to 62 years of age who have moderate to severe (scale 5-9 out of 0-9 scale) (prominent) frown lines in the glabellar area. Subject inclusion criteria included: (1) Healthy female subjects, between 35 and 70 years old, and considered to be in general good health (no physical required, based on self report); (2) Written informed consent obtained; (3) Subjects were willing to complete a medical history form; (4) Subjects have moderate to severe (scale 5-9 out of 0-9 scale) (prominent) frown lines in the glabellar area; (5) subjects were willing to comply with study instructions; and (6) Subjects must be apprised of the Health Insurance Portability and Accountability Act (HIPAA). Subject exclusion criteria—subjects with any of the following conditions were excluded from this study: (1) Use of an investigational drug or device on the face within 28 days of enrollment; (2) Subjects who have received facial Botox™ injections within the last 12 months; (3) Any facial cosmetic procedure in any planned treatment area within the last 12 months; (4) Any previous insertion of permanent material in planned treatment area; (5) Any facial cosmetic procedure planned for within the study period; (6) Any systemic disease or disorder, complicating factors or structural abnormality that would negatively affect the conduct or outcome of the study; (7) Subjects with hematological or immunologic disorders (HIV positive, AIDS and Systemic Lupus Erythematosus); (8) Female subjects who are pregnant, nursing mothers, planning a pregnancy during the course of the trial, or becomes pregnant during the study (self-reporting only, a pregnancy test is not required); (9) Subjects who have a fear of needles (needle phobia); (10) Allergic reactions to Botox™ or other type of dermatological injectables (such as fillers); and/or (11) Subjects who are unable to communicate or cooperate with the Investigator due to language problems, poor mental development, impaired cerebral function.

Figure 3:
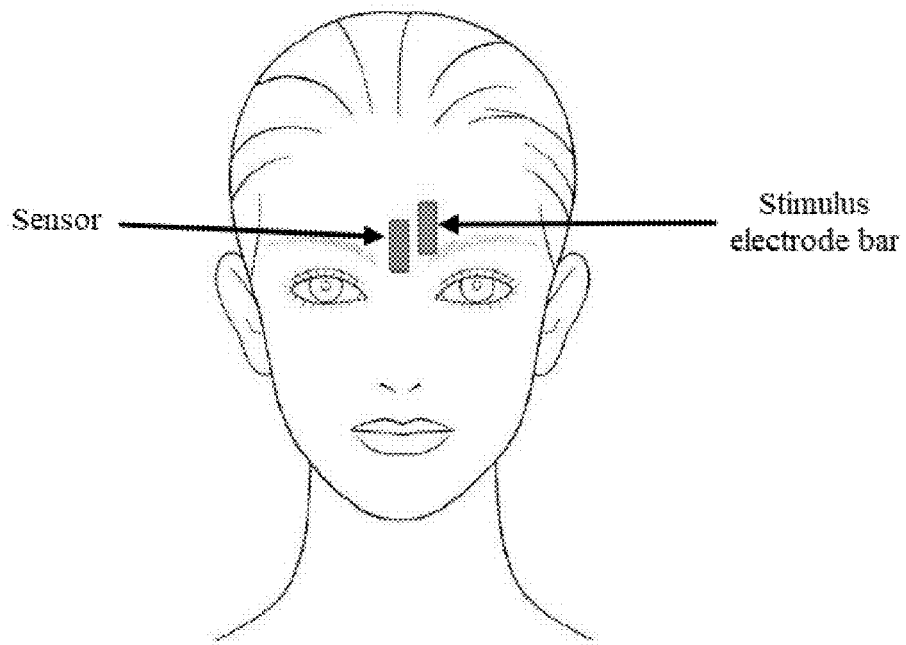

Materials and Methods: Baseline Visit—Subjects arrived at the testing facility for their baseline measurements were directed into an environmentally controlled room (70° F.+5° F., 50%+15% relative humidity) where they acclimated to the room's conditions for at least 15 minutes. Following equilibration, baseline EMG measurements were taken in triplicate in the glabellar area to measure the baseline CMAP of the Corrugator Supercilii and Procerus Muscles. To do this, a technician applied the Trigno™ wireless EMG sensor to the glabellar area. Once the sensor was attached to the subject, a series of "insult" scans were generated at two second intervals in which the amount of stimulus/energy/ insult (measured in millivolts, mV) varied each interval (typically starting at 2 mV and increasing up to a maximum of 10 mV). The stimulus was induced by placing the stimulating bar electrode (Stimulating Bar Electrode (MLADDF30) (Ad Instruments Inc., Colorado Springs, CO (USA))) in the area close to the Trigno™ sensor and powering the bar with a set energy (mV) (Stimulus Isolator FE180 (Ad Instruments Inc., Colorado Springs, CO (USA))). The scans were reviewed after each insult to determine if a proper compound motor action potential (CMAP) was observed. A typical placement of the recording device/sensor and the stimulus bar electrode on the subjects faces is illustrated in FIG. 3. Once the position of the stimulating bar (relative to the Trigno™ sensor) and stimulus strength were identified that produces the proper CMAP response, these values were recorded for that site and used throughout the study. The stimulus was set to the mV that produced the best CMAP response (based on the shape of the curve) and a total of 10 sequential scans were taken over a 33 second period with stimulus of the test site occurring every three seconds. After the 10 scans were complete, the Trigno™ sensors were removed and the subjects were instructed to return to the testing facility at their scheduled visit to receive their Botox™ injection.

In addition to the EMG measurements discussed above, clinical grading was also performed of the area for facial skin wrinkles using the following numerical scale: 0=no wrinkles; 1-3=mild wrinkles; 4-6=moderate wrinkles; and 7-9=severe wrinkles.

Facial digital photographs (frontal position only) of each subject were taken using a high-resolution digital camera (Canon EOS 5D) attached to the Canfield VISIA CR Booth (Fairfield, New Jersey). Images were captured under standard and parallel polarized lighting.

Figure 4:
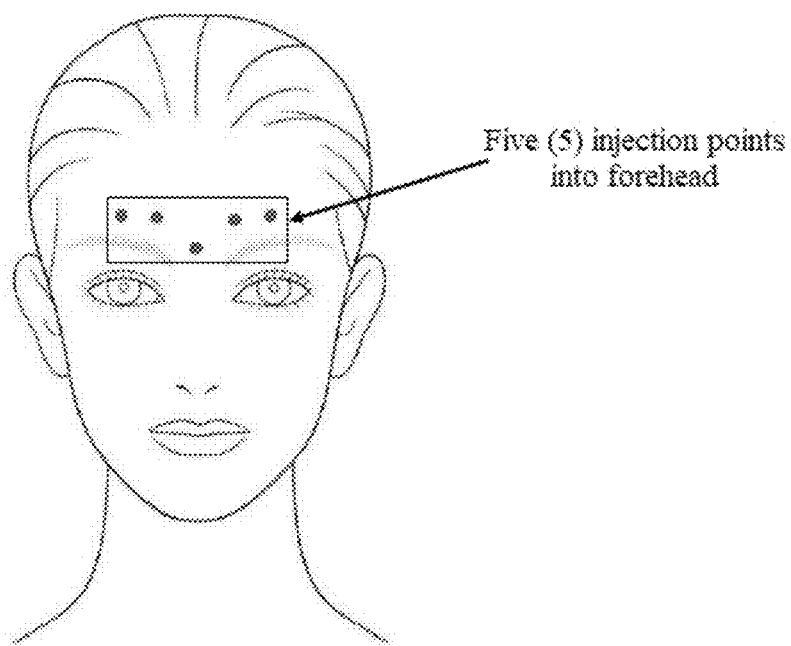

Botox™ Visit—A board certified dermatologist injected each subject with 1 unit of Botox™ (Allergan, Inc.) into each of the 5 injection points in the forehead illustrated in FIG. 4, for a total of 5 units. All post baseline time points were relative to the injection of Botox™, not baseline measurements.

Week 2 and Week 4 Visits—Subjects returned at weeks 2 and 4 were directed into an environmentally controlled room (70° F.+5° F., 50%+15% relative humidity) where they acclimated to the room's conditions for at least 15 minutes. Following acclimation, the subjects underwent EMG measurements identical to the measurements taken at baseline. The same intensity of stimulus generated by the power bar and identified at baseline as the intensity that produces the best CMAP curve were used at the week 2 and 4 time points. Additionally, visual grading for wrinkles/fine lines and photography were taken at these time points. After Week 4 measurements, the subjects were dismissed from the study.

Results: When injected intramuscularly, Botulinum Toxin attaches to receptors on muscle cells, and prevents the release of acetylcholine, preventing the contraction of the muscle cells. This can dramatically lower the response of the muscles when measured using EMG, as well as the appearance of wrinkles around the area of injection. Table 3 show the effect of the Botox™ injections on EMG/CMAP and the Clinical appearance of wrinkles.

TABLE 3

| Descriptive Stats | EMG-Area Under the Curve | | | EMG-Peak Height (mV) | | | Clinical Grading of Wrinkles | | |
|---|---|---|---|---|---|---|---|---|---|
| | Baseline | Week 2 | Week 4 | Baseline | Week 2 | Week 4 | Baseline | Week 2 | Week 4 |
| Mean | 0.6 | 0.25 | 0.36 | 24.74 | 14.25 | 16.91 | 6.2 | 4.3 | 4 |
| SD | 0.15 | 0.08 | 0.17 | 4.31 | 2.86 | 3.61 | 1.3 | 1.79 | 2.1 |
| Median | 0.64 | 0.24 | 0.31 | 26.82 | 14.24 | 15.23 | 6 | 4 | 4 |
| N | 5 | 5 | 5 | 5 | 5 | 5 | 5 | 5 | 5 |
| % Change Relative to Baseline | — | −58.33 | −40.00 | — | −42.40 | −31.65 | — | −30.64 | −35.45 |

The data from Table 3 show the change in response area (area under the curve), peak height, and clinical grading of wrinkles both before (baseline) and after (2 weeks and 4 weeks) the injection of Botox™. Subjects received Botox™ injections within two days of baseline measurements, and both subsequent visits (week 2 and week 4) were timed relative to the injection visit. The change in values for both the response area and the peak height followed the same trend—values decreased from baseline to week 2 (after the injection of Botox™), and began to rise again by the week 4 visit. The clinical assessment values for wrinkles, however, continued to decrease through the week 4 visit.

Under the conditions of the study the Botox™ had a measureable impact on EMG and clinical wrinkle assessment data and provided evidence to show that a decrease in electromyography data can detect changes in both the response area and peak height which is consistent with the decrease in the appearance of wrinkles.

All of the assays and/or methods disclosed and claimed herein can be executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method for quantitatively assessing muscle contraction of a facial muscle in a person and determining the ability of a treatment material to reduce contraction of the facial muscle, the method comprising:
   (a) applying an external electrical stimulus to facial skin sufficient to contract a facial muscle, wherein the external electrical stimulus is applied at an interval for 1 to 10 seconds and/or is applied for 2 to 20 intervals; and
   (b) measuring the contractile activity of the contracted facial muscle by measuring the compound motor action potential (CMAP) of the contracted facial muscle to obtain a first average measurement of contractile activity of the contracted facial muscle; and then
   (c) administering the treatment material by topically applying the treatment material to the facial skin; and
   (d) repeating steps (a) and (b) to obtain a second average measurement of contractile activity of the contracted facial muscle,
   wherein a decrease in contractile activity based on the second average measurement as compared to the first average measurement indicates that the treatment material reduces contraction of the facial muscle when administered to the facial skin.

2. The method of claim 1, wherein the treatment material comprises a chemical compound, a protein, a peptide, a botanical plant/plant part, or a bacteria, or combinations thereof.

3. The method of claim 2, wherein the treatment material is a protein.

4. The method of claim 3, wherein the protein is *Clostridium botulinum* toxin.

5. The method of claim 1, wherein the treatment material is comprised in a topical skin formulation.

6. The method of claim 5, wherein the topical skin formulation is an emulsion.

7. The method of claim 5, wherein the topical skin formulation is a gel.

8. The method of claim 5, wherein the topical skin formulation is an ointment.

9. The method of claim 5, wherein the topical skin formulation is a solution.

10. The method of claim 1, further comprising obtaining a first image of the facial skin prior to administering the treatment material and obtaining a second image of the skin after administering the treatment material.

11. The method of claim 10, wherein the first and second images are used to determine the effectiveness of the treatment material to reduce the appearance of rhytides present on the facial skin.

12. The method of claim 1, wherein measuring the contractile activity of the contracted facial muscle further comprises measuring the electrical activity of the contracted facial muscle.

13. The method of claim 1, wherein measuring the contractile activity of the contracted facial muscle further comprises surface electromyography.

14. The method of claim 1, wherein the external electrical stimulus is generated from a conductive material having a square shape, a rectangular shape, a circular shape, or a triangular shape.

15. The method of claim 1, wherein the method for quantitatively assessing muscle contraction of the facial muscle does not rely on the use of voluntary contractions of the facial muscle by the person.

16. The method of claim 1, wherein the facial muscle is a glabellar complex muscle, an orbicularis oculi muscle, a depressor muscle, or a frontalis muscle, or any combination thereof.

17. The method of claim 1, wherein the facial skin includes a rhytide.

* * * * *